United States Patent [19]

Babington et al.

[11] 4,287,196

[45] Sep. 1, 1981

[54] METHOD OF INHIBITING PROLACTIN SECRETION

[75] Inventors: Ronald G. Babington, Denville, N.J.; F. Eugene Harrington, Albuquerque, N. Mex.; William J. Houlihan, Mt. Lakes, N.J.

[73] Assignee: Sandoz, Inc., E. Hanover, N.J.

[21] Appl. No.: 124,810

[22] Filed: Feb. 26, 1980

[51] Int. Cl.$^3$ ................... A61K 31/33; A61K 31/505
[52] U.S. Cl. ..................................... 424/251; 424/244
[58] Field of Search ................ 424/244, 250, 251, 274

[56] References Cited

U.S. PATENT DOCUMENTS

| | | | |
|---|---|---|---|
| 3,444,181 | 5/1969 | Houlihan | 424/251 X |
| 3,755,360 | 8/1973 | Houlihan | 424/274 X |
| 3,763,178 | 10/1973 | Sulkowski | 424/274 X |
| 3,867,374 | 2/1975 | Reynold et al. | 424/244 X |
| 4,202,897 | 5/1980 | Babington et al. | 424/250 |

*Primary Examiner*—Frank Cacciapaglia, Jr.
*Attorney, Agent, or Firm*—Gerald D. Sharkin; Robert S. Honor

[57] ABSTRACT

Certain known pyrimido[2,1-a]isoindoles and diazepino[2,1-a]isoindoles, e.g., 7-(p-chlorophenyl)-7-hydroxy-2,3,4,5-tetrahydro-7H-[1,3]-diazepino[2,1-a]isoindoles, are useful for inhibiting prolactin secretion.

7 Claims, No Drawings

METHOD OF INHIBITING PROLACTIN SECRETION

This invention relates to the use of known substituted [2,1-a]isoindoles as prolactin secretion inhibition agents.

More particularly, it has now been found that the effect against secretion of prolactin by certain compounds with which this invention is concerned is surprisingly partly because of the relatively low level of undesirable side effects of such compounds. For instance, these agents of formula I below have a high level of prolactin secretion inhibition activity despite their relatively low level of activity as central nervous system stimulants.

The isoindoles with which this invention is concerned may be represented by the following structural formula

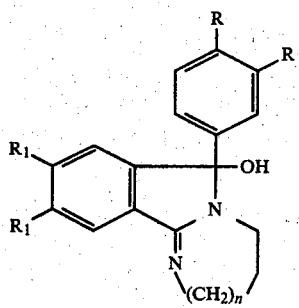

where
n represents 1 or 2,
each R, independently, represents hydrogen or halo of atomic weight about 19 to 36, and
each $R_1$, independently, represents hydrogen or said halo, provided that when one $R_1$ is halo, the other is hydrogen.

or a pharmaceutically acceptable acid addition salt thereof.

As will be seen, the pyrimido[2,1-a]isoindoles with which this invention is concerned pertain to compounds of the formula

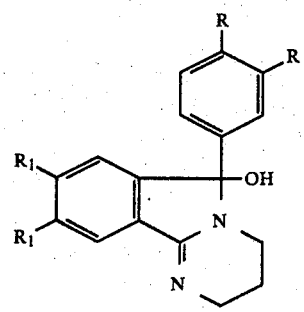

whereas the diazepino[2,1-a]isoindoles are of the formula

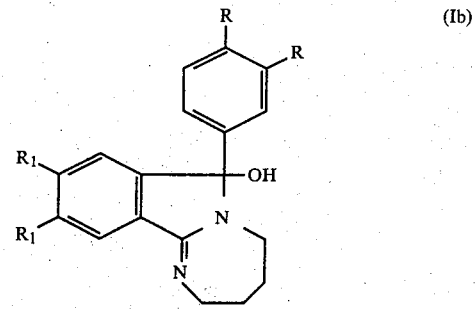

where R and $R_1$ have the definitions set out above.

The compounds of formula (I) are known and may be prepared according to methods disclosed in the art, e.g., U.S. Pat. Nos. 3,763,178 and 3,755,360. The present invention contemplates only the novel use of such compounds, particularly as agents useful for prolactin secretion inhibition in animals, especially in mammals such as primates.

Particularly preferred compounds in connection with this invention are 7-(p-chlorophenyl)-7-hydroxy-2,3,4,5-tetrahydro-7H-[1,3]diazepino[2,1-a]isoindole and 6-(p-chlorophenyl)-6-hydroxy-2,3,4,6-tetrahydropyrimido[2,1-a]isoindole. An alternate nomenclature, applicable to all the compounds of formula (I), may be illustrated by referring to the last named compound as 6-(p-chlorophenyl)-2,3,4,6-tetrahydropyrimido[2,1-a]isoindol-6-ol.

The compounds of formula (I) are useful as prolactin secretion inhibitors as indicated by noting serum levels of prolactin after oral administration to rats of 0.01–10 mg/kg of active agent. Male Sprague-Dawley rats weighing 220–280 grams are used to determine the effects of drug on serum levels of prolactin. The drug is orally administered to three animals per experiment in 2% carboxy methyl cellulose. Two or three experiments were run for each compound tested.

At the time of drug administration three control rats are sacrificed by decapitation. At 30 minutes following drug treatment, groups of three controls and animals treated with drug are also sacrificed by decapitation. Blood samples are collected at autopsy, allowed to clot, and the serum separated by centrifugation. Equal parts of serum samples are pooled and assayed for prolactin levels using radioimmunological techniques disclosed by Niswender, G. D., et al., Proc. Soc. Exper. Biol. & Med., 130: 793, 1969; and Neil, J. J., et al., Endocrinology, 88: 548, 1971.

For use as prolactin secretion inhibition agents, compounds (I) may be administered as such or admixed with conventional pharmaceutical carriers. They may be administered orally in such forms as tablets, dispersible powders, granules, or capsules, or as oral liquids, e.g., oral liquid suspensions, syrups and elixirs, and parenterally as solutions, suspensions, dispersions, emulsions, and the like, e.g., a sterile injectable aqueous suspension or as suppositories, etc.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly are included within the scope of the invention. Representative of such salts are the mineral acid salts, such as the hydrochloride, hydrobromide, sulfate, phosphate and the like and the organic acid salts, such as the succinate, maleate, fumarate, acetate, p-toluenesulfonate, and the like.

The dosage of compounds (I) employed for prolactin secretion inhibition activity may vary depending on the particular compound (I) employed and the severity of the condition being treated. However, in general, satisfactory results may be obtained when the compounds (I) are administered, preferably orally, at a daily dosage of from about 0.01 milligram to about 10 milligrams per kilogram of animal body weight, preferably given in divided doses two to four times a day, or in sustained release form. For most large mammals, the total daily dosage of compounds (I) is from about 0.05 to 5 milligrams. Dosage forms suitable for internal use comprise from about 0.0125 to about 2.5 milligrams of the active compound (I) in intimate admixture with a solid or liquid pharmaceutically acceptable carrier or diluent.

The preferred pharmaceutical compositions from the standpoint of preparation and ease of administration are tablets or capsules containing about 0.1 to 2 milligrams of compound (I).

Of significance is the relatively low level of undesirable side effects and secondary activities of the instant prolactin secretion inhibitors of formula (I). In particular, it has been found that said compounds have a relatively low level of central nervous system activity and that, for instance, the anorexic and anti-depressant activities of these compounds are low relative to the corresponding prolactin secretion inhibition activity.

EXAMPLES 1 AND 2

Tablets and Capsules Suitable For Oral Administration

Tablets and capsules containing the ingredients indicated below may be prepared by conventional techniques and are useful in inhibiting prolactin secretion at a dose of one tablet or capsule two to four times a day.

| INGREDIENT | WEIGHT | |
|---|---|---|
|  | Tablet | Capsule |
| 6-(p-chlorophenyl)-2,3,4,6-tetra-hydropyrimido[2,1-a]isoindol-6-ol | 0.5 | 0.5 |
| tragacanth | 10 | — |
| lactose | 247 | 299.5 |
| corn starch | 25 | — |
| talcum | 15 | — |
| magnesium stearate | 2.5 | — |

What is claimed is:
1. A method for inhibiting prolactin secretion which comprises administering to a mammal in need of said treatment an amount sufficient to inhibit prolactin secretion of a compound of the formula

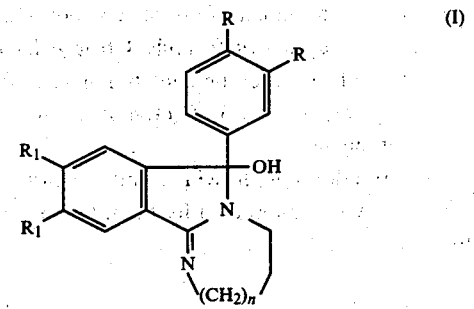

where n represents 1 or 2,
each R, independently, represents hydrogen or halo of atomic weight about 19–36, and
each $R_1$, independently, represents hydrogen or said halo, provided that when one $R_1$ is halo, the other is hydrogen, or
a pharmaceutically acceptable acid addition salt thereof.

2. A method according to claim 1 wherein n represents 1.

3. A method according to claim 1 wherein n represents 2.

4. A method according to claim 2 in which the compound is 6-(p-chlorophenyl)-2,3,4,6-tetrahydropyrimido[2,1-a]isoindol-6-ol.

5. A method according to claim 3 in which the compound is 7-(p-chlorophenyl)-7-hydroxy-2,3,4,5-tetrahydro-7H-[1,3-]diazepino[2,1-a]isoindole.

6. A method according to claim 1 wherein the compound is administered to a mammal in need of said treatment at a daily dose of from about 0.05 milligrams to about 5 milligrams.

7. A method according to claim 1 wherein the compound is administered to a mammal in need of said treatment in a unit dosage form comprising said compound to the extent of from about 0.0125 milligrams to about 2.5 milligrams per unit dosage.

* * * * *